United States Patent
Knox et al.

(10) Patent No.: US 9,111,427 B2
(45) Date of Patent: Aug. 18, 2015

(54) CHAMBER CONDITION

(75) Inventors: Ron Knox, Victoria (AU); Karl Boettger, Mount Waverley (AU)

(73) Assignee: Xtralis Technologies Ltd (BS)

( * ) Notice: Subject to any disclaimer, the term of this patent is extended or adjusted under 35 U.S.C. 154(b) by 334 days.

(21) Appl. No.: 13/382,746

(22) PCT Filed: Jul. 7, 2010

(86) PCT No.: PCT/AU2010/000871
§ 371 (c)(1),
(2), (4) Date: Mar. 6, 2012

(87) PCT Pub. No.: WO2011/003145
PCT Pub. Date: Jan. 13, 2011

(65) Prior Publication Data
US 2012/0154161 A1    Jun. 21, 2012

(30) Foreign Application Priority Data
Jul. 7, 2009    (AU) .............................. 2009903184

(51) Int. Cl.
| | |
|---|---|
| G08B 17/10 | (2006.01) |
| G08B 21/00 | (2006.01) |
| G08B 23/00 | (2006.01) |
| G05B 23/02 | (2006.01) |
| G08B 5/22 | (2006.01) |
| H04Q 1/30 | (2006.01) |
| G08C 19/16 | (2006.01) |

(Continued)

(52) U.S. Cl.
CPC .............. *G08B 17/107* (2013.01); *G01N 21/53* (2013.01); *G08B 29/24* (2013.01)

(58) Field of Classification Search
CPC .... G08B 17/107; G08B 17/10; G08B 29/145; G08B 29/20
USPC ................................................ 340/607, 693.6
See application file for complete search history.

(56) References Cited

U.S. PATENT DOCUMENTS

| | | | |
|---|---|---|---|
| 3,787,122 A | 1/1974 | Lepper et al. | |
| 3,809,913 A | 5/1974 | Prellwitz | |

(Continued)

FOREIGN PATENT DOCUMENTS

| | | |
|---|---|---|
| CN | 1075549 A | 8/1993 |
| EP | 1967843 | 9/2008 |

(Continued)

OTHER PUBLICATIONS

"Australian Application No. 2009903184, Australian Patent Office International-Type Search Report mailed Mar. 30, 2010", 2 pgs.

(Continued)

*Primary Examiner* — Steven Lim
*Assistant Examiner* — Muhammad Adnan
(74) *Attorney, Agent, or Firm* — Schwegman Lundberg & Woessner, P.A.

(57) ABSTRACT

A particle detector including a chamber, a first aspirator, a sensor(s), a controller and clean air supply. The controller, when in a detecting mode, receives an indicative signal from the sensor and applies logic to the indicative signal to generate a further signal, and when in the purge mode controls substantial purging of the chamber of sample fluid with clean fluid from the clean fluid supply. The controller receives the indicative signal when the chamber is so purged and if necessary adjusts the logic in response thereto.

27 Claims, 7 Drawing Sheets

(51) Int. Cl.
*G08B 17/107* (2006.01)
*G01N 21/53* (2006.01)
*G08B 29/24* (2006.01)

(56) References Cited

U.S. PATENT DOCUMENTS

| | | | |
|---|---|---|---|
| 4,155,651 A | 5/1979 | Malone | |
| 4,583,859 A | 4/1986 | Hall, II | |
| 4,616,928 A * | 10/1986 | Leavitt et al. | 356/338 |
| 4,617,560 A * | 10/1986 | Gutmann | 340/628 |
| 5,001,463 A * | 3/1991 | Hamburger | 340/627 |
| 5,163,332 A | 11/1992 | Wong | |
| 5,477,218 A * | 12/1995 | Manmoto et al. | 340/630 |
| 5,543,777 A | 8/1996 | Vane et al. | |
| 5,946,091 A | 8/1999 | Yufa | |
| 6,184,537 B1 * | 2/2001 | Knox et al. | 250/574 |
| 6,285,291 B1 * | 9/2001 | Knox et al. | 340/634 |
| 2007/0176783 A1 * | 8/2007 | Knox et al. | 340/607 |
| 2009/0128810 A1 | 5/2009 | Bates | |
| 2011/0058167 A1 * | 3/2011 | Knox et al. | 356/338 |
| 2012/0050030 A1 * | 3/2012 | Murphy et al. | 340/514 |

FOREIGN PATENT DOCUMENTS

| | | | |
|---|---|---|---|
| GB | 2091485 A | 7/1982 | |
| GB | 2261502 A * | 5/1993 | G01N 21/47 |
| GB | 2309076 | 7/1997 | |
| GB | 2 327 752 | 2/1999 | |
| JP | S57-189041 | 11/1982 | |
| JP | 59-136639 A | 8/1984 | |
| JP | 59-151040 A | 8/1984 | |
| JP | 59-192940 A | 11/1994 | |
| JP | 07-151680 A | 6/1995 | |
| JP | 08-271425 A | 10/1996 | |
| JP | 11312278 A | 11/1999 | |
| JP | 2000-509503 A | 7/2000 | |
| JP | 2007-248388 A | 9/2007 | |
| JP | 2008-234416 A | 10/2008 | |
| NZ | 250497 A | 3/1998 | |
| WO | WO-97/42485 A1 | 11/1997 | |
| WO | WO-97/42486 A1 | 11/1997 | |
| WO | WO-2009/062256 | 5/2009 | |

OTHER PUBLICATIONS

"International Application No. PCT/AU2010/000871, International Search Report and Written Opinion mailed Aug. 9, 2010", 6 pgs.

"Machine Translation of JP 08-271425A, published Oct. 18, 1996", 14 pgs.

"Machine Translation of JP 2007-248388A, published Sep. 27, 2007", 24 pgs.

"Machine Translation of JP 2008-234416A, published Oct. 2, 2008", 12 pgs.

* cited by examiner

CHAMBER CONDITION

PRIORITY CLAIM TO RELATED APPLICATIONS

This application is a national stage application under 35 U.S.C. §371 of PCT/AU2010/000871, filed Jul. 7, 2010, and published as WO 2011/003145 A1 on Jan. 13, 2011, which claims priority to Australian Application No. 2009903184, filed Jul. 7, 2009, which applications and publication are incorporated herein by reference and made a part hereof in their entirety, and the benefit of priority of each of which is claimed herein.

FIELD OF THE INVENTION

The invention relates to particle detection. The following description focuses on smoke detectors, and in particular optical smoke detectors, however the skilled person will appreciate that the invention has broader application.

For the avoidance of doubt, 'particle detection' and like terms are used herein to refer to the detection of solid and/or liquid particles.

BACKGROUND OF THE INVENTION

Various smoke detectors include a chamber through which a sample of air is drawn and studied to determine if particles are present. Over time the accumulation of dust and debris on surfaces within the detection chamber can affect the operation of the detector.

By way of example, scattering light detectors include a light source arranged to project a beam across the detection chamber. A photoelectric sensor is arranged so that its field of view is traversed by a portion of the beam. The photoelectric sensor receives light scattered from the beam due to the presence of particles in the detection chamber. Over time dust and debris can accumulate on surfaces within the detection chamber and reflect light towards the photoelectric sensor thereby providing a false indication of particles in the detection chamber. Dust and debris may also settle on the light source and/or the photoelectric sensor thereby obscuring the transmission and receipt of light and reducing the sensitivity of the detector.

One approach to addressing these problems involves the use of an 'air barrier'. An air barrier is created by directing one or more streams of clean air into the detection chamber to flow over the critical components, such as the light source, the photoelectric sensor and walls within the field of view of the photoelectric sensor, to prevent dust and debris accumulating thereon.

Aspirated smoke detectors employ a fan, known as an aspirator, to draw air to be studied through the detection chamber. The air to be studied enters the chamber via an inlet(s). A desirable implementation of the air barrier concept employs a filter(s) to create the clean air. The filter is arranged in parallel to the inlet, whereby the clean air is drawn through the filter and into the detection chamber by the aspirator. A common stream of air, e.g. from a network of pipes, may be divided into two portions—one portion being filtered to create the clean air, and the other portion entering the chamber to be studied.

Another approach to addressing the problems associated with the accumulation of dust and debris in the detection chamber is to obtain a measurement associated with light reflected from the accumulated dust and debris, known as 'background light', and to adjust the detection criteria applied to the signal received from the photoelectric sensor in response to the background light. One approach to obtaining a measure of background light involves the use of a second photoelectric sensor within the detection chamber. The second photoelectric sensor is arranged so that its field of view does not include the beam. Signals from the second photoelectric sensor are thereby indicative of light reflected within the detection chamber rather than light scattered directly from the beam.

The abstract of Japanese patent application 59192940 is entitled Smoke Meter with Purging Device and describes filling a measuring device with clean air and measuring opaqueness in the clean atmosphere to perform calibration. The described device includes a dedicated blower to supply clean air to the detection chamber. A valve controlled by depressible switches is used to close the intake tube to halt the flow of discharge gases to the detection chamber prior to the purging operation.

New Zealand patent 250497 is concerned with preventing fire suppression measures being activated in response to false alarms. It describes an operating syntax applicable to aspirated smoke detectors. When an alarm condition is detected the chamber is purged with clean air and a background 'smoke' signal is measured. If the background reading does not fall below a predetermined threshold a detector fault is indicated. If the background 'smoke' falls below the predetermined threshold, the system waits for the detected smoke level to rise above a further threshold before triggering the fire suppression systems.

It is an object of the invention to provide an improved particle detector.

SUMMARY OF THE INVENTION

Various aspects of the invention relate to methods of, and apparatus for, purging a detection chamber to obtain a background reading which can be used for calibration.

In one aspect the invention provides a particle detector including:
a chamber including at least one sample inlet for receiving sample fluid, at least one clean fluid inlet for receiving clean fluid, and at least one fluid outlet;
a first aspirator for moving the sample fluid through the chamber;
one or more sensors for detecting, and providing a sensor signal indicative of, particles in the chamber;
a controller having a detecting mode and a purge mode,
a clean fluid supply for supplying clean fluid to the clean fluid inlet, the clean fluid supply and clean fluid inlet cooperating, when in the detecting mode, to direct clean fluid into the chamber to prevent contamination by dust and debris of one or more components the contamination of which would reduce the accuracy of the particle detector; and
the controller, when in the detecting mode, receiving the sensor signal and applying logic to the sensor signal to generate a further signal, and when in the purge mode controlling substantial purging of the chamber of sample fluid with clean fluid from the clean fluid supply;
the controller receiving the sensor signal when the chamber is so purged and if necessary adjusting the logic in response thereto.

The first aspirator may be deactivated when in the purge mode. The clean fluid supply may drive clean fluid to the chamber. In the purge mode the clean fluid supply may be activated to drive clean fluid to the chamber.

Preferably the clean fluid supply includes a filter, for filtering fluid to produce clean fluid, and a dedicated clean fluid aspirator for moving the clean fluid, the dedicated clean fluid aspirator being downstream of the filter to avoid exposure to unfiltered fluid. According to preferred forms of the invention, when in the detecting mode, the dedicated clean fluid aspirator is substantially inactive and the first aspirator moves fluid through the filter. Advantageously, in at least a portion of the purge mode, the first aspirator is inactive to halt the flow of sample fluid though the chamber and the dedicated clean fluid aspirator is active to drive clean fluid into the chamber.

The detector preferably includes plumbing for dividing a stream of fluid (e.g. from a piping network) into two or more portions, and directing one portion to the clean fluid supply to be filtered to form clean fluid, and directing another portion to the chamber to form the sample fluid.

Advantageously the controller may automatically purge the chamber and if necessary adjust the logic. By way example, the controller may be configured to so purge and if necessary adjust periodically; the interval between adjustments could be variable but preferably it is fixed, and most preferably is about 28 days. The purging and adjustment operations are preferably conducted at the same time of day, e.g. during working hours.

The detector may be an optical detector, such as a light scattering detector including a light source, for projecting light (e.g. a beam) through the chamber, and a photoelectric device having a field of view intersecting the projected light such that the photoelectric device receives light scattered from the projected light by particles present in the chamber; the photoelectric device forming the sensor.

The detector is preferably a smoke detector in which case the sensor signal preferably provides an indication of the smoke level. The further signal may be, or include, an alarm signal. The logic may include an alarm threshold. The controller may be configured such that the transition from the detection mode to purge mode is conditional on the indicative signal. For example the detector may be configured to not enter the purge mode if the indicative signal is at or above a start purge threshold. The start purge threshold preferably corresponds to a particle concentration less than, and most preferably about 50%, of the alarm threshold.

The controller preferably stores a plurality of measurements based on the indicative signal over an interval of time when the chamber is purged. The controller may be configured to generate a fault signal if the indicative signal when the chamber is purged is too low, too high, too variable, and/or too different from the indicative signal during the previous purging and adjusting operation. The logic may include subtracting a measure of background light from the indicative signal. The adjustment of the logic may include averaging the stored indicative signals to calculate a new measure of background light.

This aspect of the invention also provides a method of operating a particle detector; the particle detector including: a chamber having: at least one sample inlet for receiving sample fluid, at least one clean fluid inlet for directing clean fluid into the chamber to prevent contamination by dust and debris of one or more components the contamination of which would reduce the accuracy of the particle detector, and at least one fluid outlet; and one or more sensors for detecting, and providing a sensor signal indicative of, particles in the chamber; the method including when in a detecting mode: moving sample fluid through the chamber; receiving the sensor signal to detect particles in the chamber; and applying logic to the sensor signal to generate a further signal; and when in a purge mode: substantially purging the chamber of sample fluid with clean fluid via the clean fluid inlets; and receiving the sensor signal when the chamber is so purged; and if necessary adjusting the logic in response thereto.

In another aspect the invention provides a particle detector including: a chamber including at least one sample inlet for receiving sample fluid, and at least one fluid outlet; a first aspirator for moving the sample fluid through the chamber; one or more sensors for detecting, and providing a sensor signal indicative of, particles in the chamber; a clean fluid supply, the clean fluid supply including a filter, for filtering fluid to produce clean fluid, and a dedicated clean fluid aspirator for moving the clean fluid, the dedicated clean fluid aspirator being downstream of the filter to avoid exposure to unfiltered fluid; and a controller having an detecting mode and a purge mode: the controller, when in the detecting mode, receiving the sensor signal and applying logic to the sensor signal to generate a further signal, and when in the purge mode controlling substantial purging of the chamber of sample fluid with clean fluid from the clean fluid supply; wherein the controller receives the sensor signal when the chamber is so purged, and if necessary adjusts the logic in response thereto.

This aspect of the invention also provides a method of operating a particle detector; the particle detector including: a chamber including at least one sample inlet for receiving sample fluid and at least one fluid outlet; one or more sensors for detecting, and providing a sensor signal indicative of, particles in the chamber; and a clean fluid supply, the clean fluid supply including a filter, for filtering fluid to produce clean fluid, and a dedicated clean fluid aspirator for moving the clean fluid, the dedicated clean fluid aspirator being downstream of the filter to avoid exposure to unfiltered fluid; the method including when in a detecting mode: moving sample fluid through the chamber; receiving the sensor signal to detect particles in the chamber; and applying logic to the sensor signal to generate a further signal; and when in a purge mode: substantially purging the chamber of sample fluid with clean fluid from the clean fluid supply; and receiving the sensor signal when the chamber is so purged; and if necessary adjusting the logic in response thereto.

DETAILED DESCRIPTION OF THE EMBODIMENTS

Figure 1:
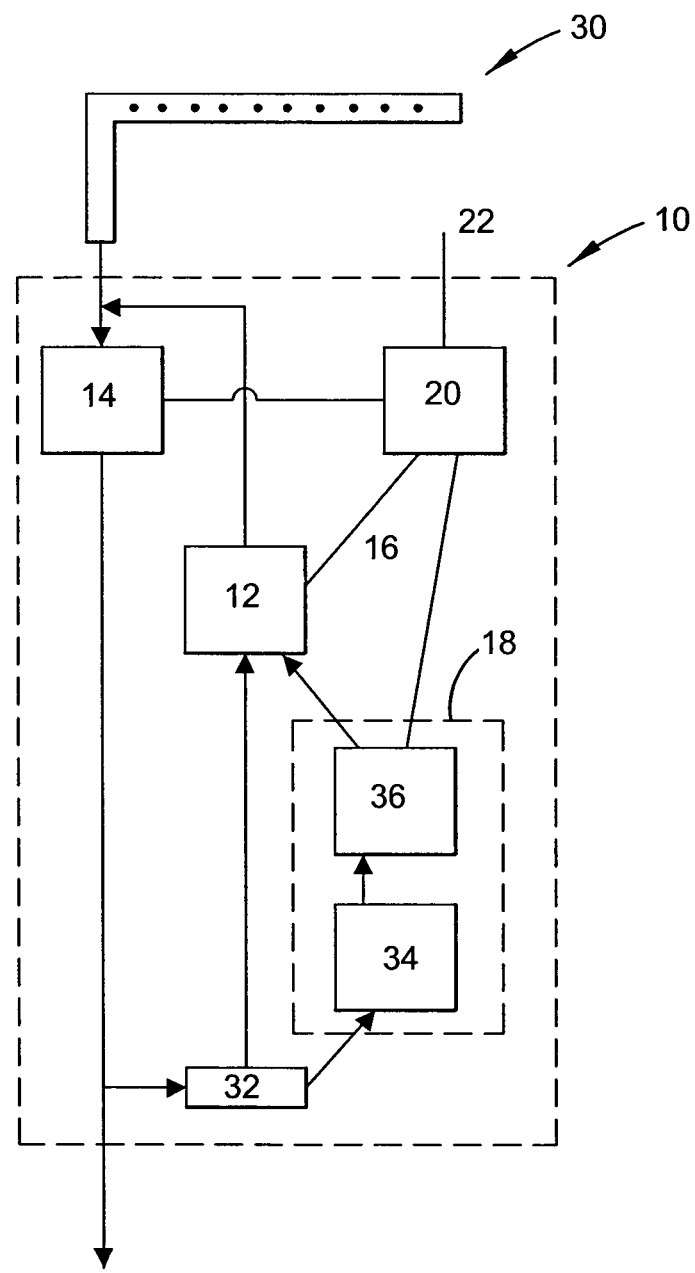
FIG. 1 is a schematic illustration of a particle detector in accordance with a preferred embodiment of the invention.

The particle detector 10 of FIG. 1 is a smoke detector in accordance with a preferred embodiment of the invention. The particle detector 10 includes a detection chamber 12, an aspirator 14, a controller 20, a plumbing fitting 32 and a clean air supply 18.

The aspirator 14 is a centrifugal fan and is controlled by the controller 20. In normal operation the aspirator 14 draws air from a sampling space, e.g. a room, via the pipe network 30.

The particle detector 10 includes a plumbing fitting 32 which receives a stream of air from the exhaust of aspirator 14. The received stream of air is a small portion of the air passing through the aspirator and is referred to as a sample. The plumbing fitting 32 divides the stream of air into two portions. The plumbing fitting 32 directs one portion of air to the detection chamber 12 and a second portion of air to the clean air supply 18. The air directed to the detection chamber is not filtered and is referred to as 'sample air'.

The clean air supply 18 includes a filter 34 to filter from the air substantially all of the particles, or at least substantially all of the particles within a particle size range of interest, to create clean air. The clean, filtered, air is directed from the clean air supply 18 to the detection chamber 12.

Figure 2:
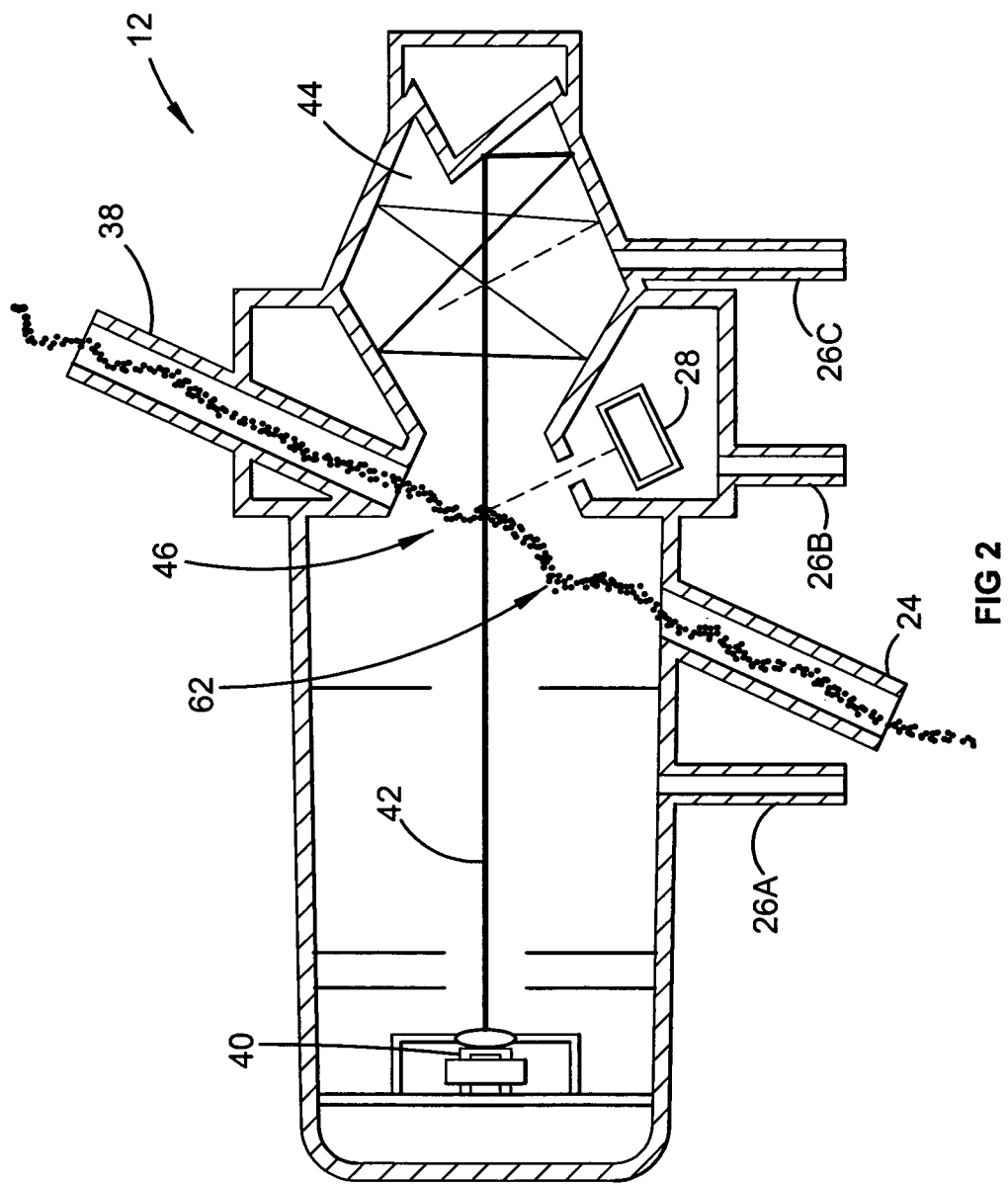
FIG. 2 is a schematic axial cross section view of the detection chamber of the particle detector of FIG. 1.

Referring to FIG. 2, the detection chamber 12 includes an inlet 24 for receiving the sample air from the plumbing fitting 32, and inlets 26A, 26B and 26C for receiving the clean, filtered, air from the clean air supply 18. The detection chamber 12 includes an outlet 38 in communication with the intake of the aspirator 14.

The sample air entering the detection chamber 12 via the inlet 24 and the clean air entering the detection chamber 12 via the inlets 26A, 26B and 26C is drawn from the detection chamber 12 by the aspirator 14 via the outlet 38 as a combined flow. As such, a stream of sample air 62, which is potentially carrying particles, traverses the detection chamber 12 between the inlet 24 and the outlet 38.

The detection chamber 12 includes a light source 40 arranged to project a beam of light 42 across the detection chamber 12. The beam 42 traverses the chamber and is dissipated in light dump 44. A photoelectric device in the form of a photodiode 28 is mounted in a sub chamber of the detection chamber 12.

The detection chamber 12 is configured so that the beam 42, the stream of sample air 62 and a field of view of the photodiode 28 coincide at a region of interest 46. The photodiode 28 is thereby arranged to receive light scattered from beam 42 by particles carried by the stream of sample air 62.

The inlets 26A, 26B and 26C are arranged to prevent dust and debris carried by the sample air from contaminating critical components the contamination of which would reduce the accuracy of the particle detector. Inlet 26A provides a stream of clean air between the inlet 26A and the outlet 38 thus creating a shield to prevent dust and debris reaching the light source 40. Inlet 26B is arranged to direct a stream of clean air over the photodiode 28 to prevent dust and debris settling thereon; and inlet 26C is arranged to prevent dust and debris settling in the light dump.

As the skilled person will appreciate, the relative impedance of the two flow paths as determined by the impedance of various components including the plumbing fitting 32, the clean air supply 18 and the inlets 24, 26A, 26B and 26C must be balanced so that appropriate proportions of sample air and clean air are delivered to the detection chamber 12.

The controller 20 receives a sensor signal 16 indicative of particles in the stream of sample fluid 62 from photodiode 28. In a detection mode the controller 20 applies logic to the sensor signal 16 to produce a further signal 22. The logic includes subtracting a measure of background light to so that the signal 22 is indicative of the concentration of particles in the stream of sample fluid 62.

The logic also includes an alarm threshold. If the concentration of particles in the stream of sample fluid 62 rises above the alarm threshold the controller responds by sending a further signal 22 including an alarm signal. If the sensor signal 16 falls below a second and lower predetermined threshold the further signal 22 includes a fault signal.

The clean air supply 18 includes, in addition to the filter 34, an aspirator 36 positioned downstream of the filter 34. Being positioned downstream of the filter 34, the aspirator 36 is exposed to clean, filtered, air rather than sample air and is thereby saved from being fouled by dust and debris carried in the unfiltered air. This allows the aspirator 36 to be a relatively small lightweight unit and to remain dormant for some time without "clagging up".

In an alternative embodiment, not illustrated, the system of FIG. 1 can be modified to place a valve in the direct airflow path to the detection chamber 12, so that the sample air supply to the chamber can be cut off when the detector enters the purge mode. In this case the dedicated clean air fan 36 could optionally be optionally omitted. With this arrangement, when the system is in purge mode, the valve to the chamber 12 is closed and the main aspirator 14 draws air through the clean air filter 34 and into the chamber, thereby filling the chamber 12 with clean air and purging the chamber 12 of sample air. A background measurement can then be taken as described elsewhere herein. To re-enter the detection mode the valve is re-opened and sample air is again drawn into the chamber 12. In detecting mode the main aspirator will draw both the sample flow and clean air supply through the chamber 12.

In use the particle detector is configured to have multiple modes of operation including a detecting mode in which ordinary particle detection operation is performed and a purge mode in which the detection chamber 12 is flushed with clean air and calibration processes are performed.

Figure 5A:
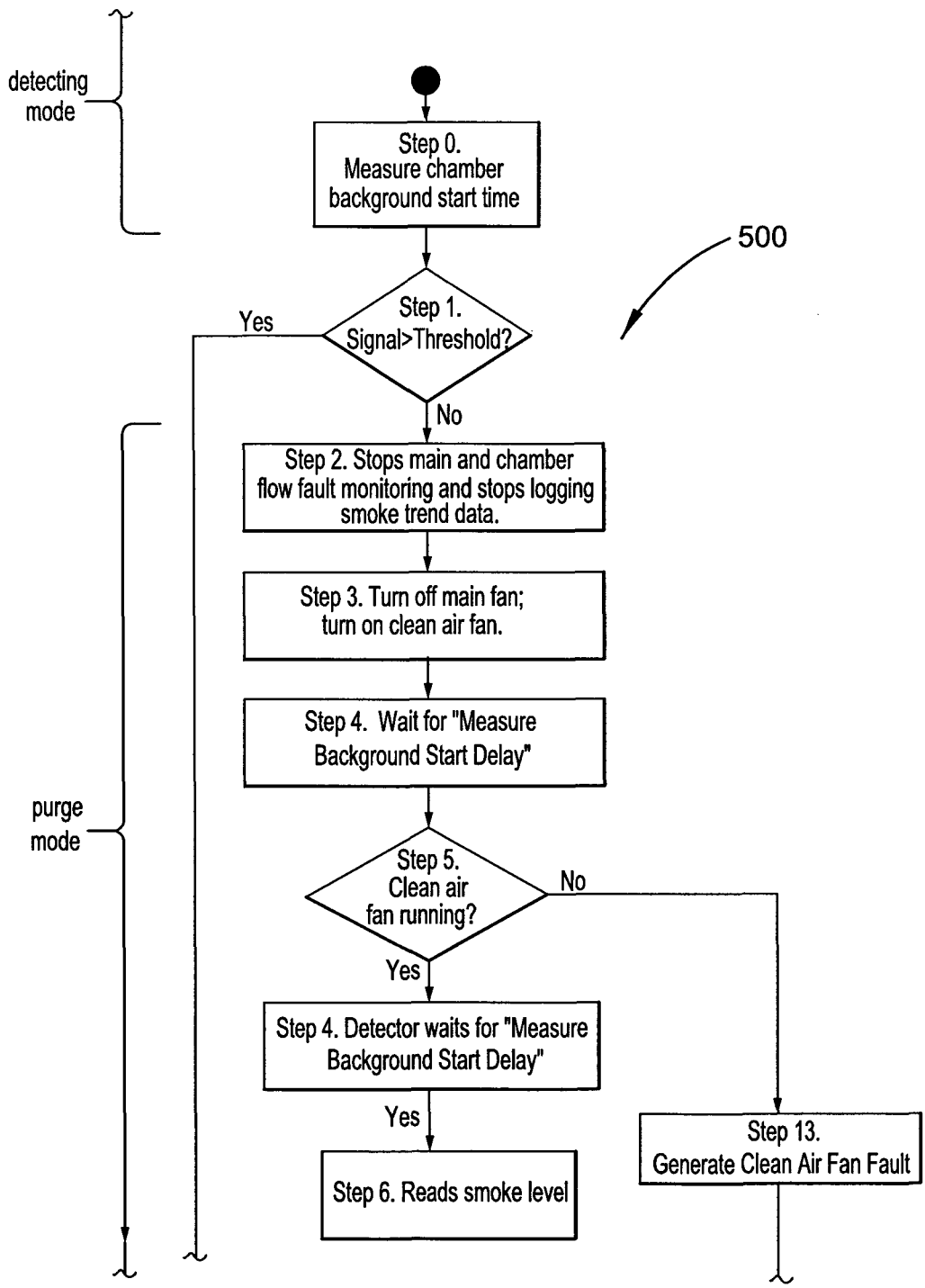
FIGS. 5A and 5B are together a flowchart illustrating the operation of the controller of the particle detector of FIG. 1.
Figure 5B:
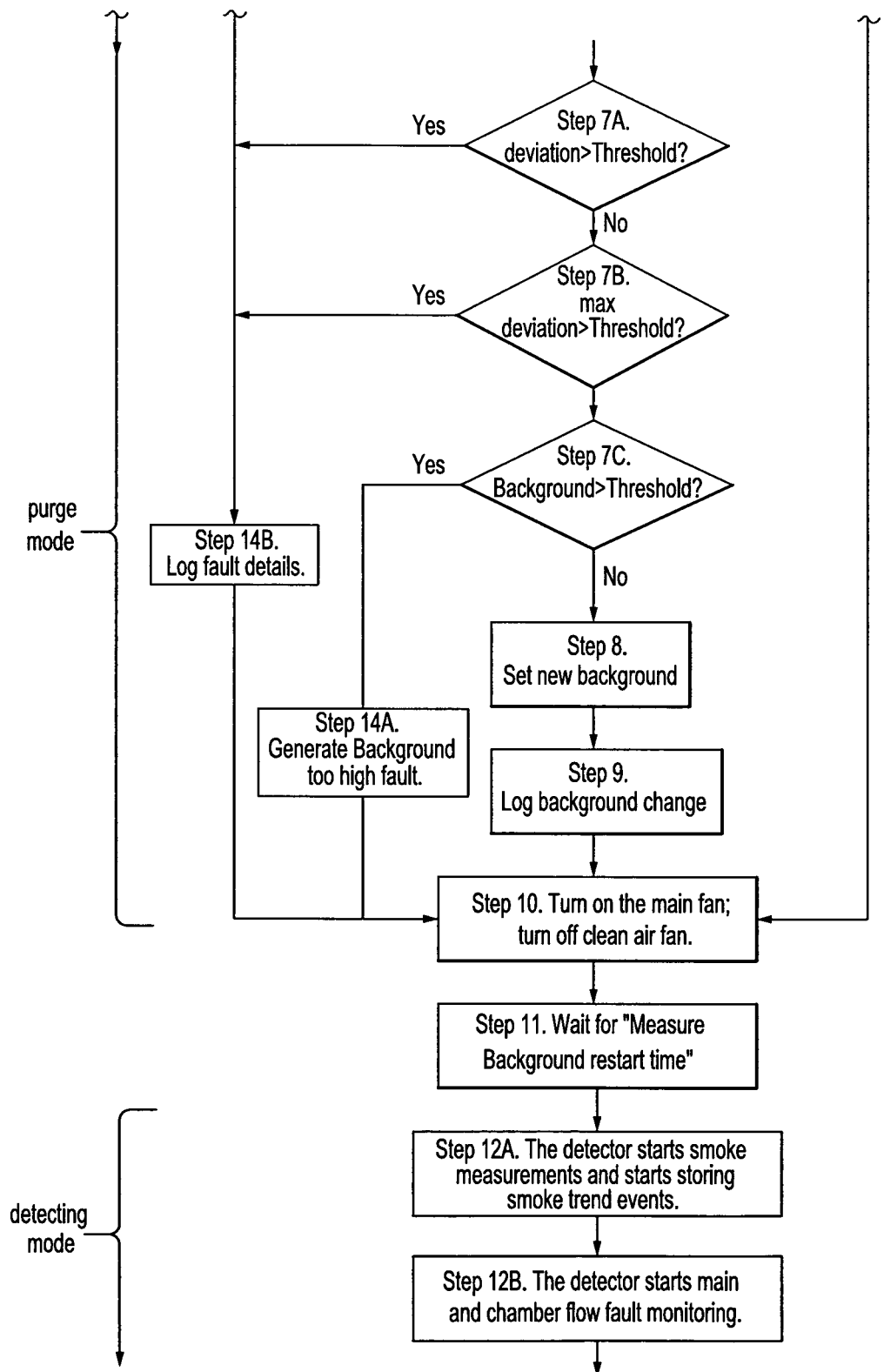

Detail of one operating method for such a detector are illustrated diagrammatically in the flow-chart of FIGS. 5A and 5B. The process 500 starts with the detector 10 operating in its detecting mode.

The controller 20 is configured or programmed to transition from the detecting mode to a purge mode once every 28 days at predetermined measure chamber background start times (see FIG. 5A; Step O). Before entering the purge mode the controller 20 first checks whether an alarm signal is imminent (step 1). In this embodiment the controller checks whether an alarm signal is imminent by comparing the sensor signal 16 to a threshold. The controller 20 only enters the purge mode if the indicative signal 16 corresponds to less than 50% of the alarm threshold.

If the sensor signal is below the threshold the controller enters the purge mode and the controller stops main and chamber flow fault monitoring and stops logging smoke trend data (step 2). This prevents a low flow fault from being raised when the main fan is stopped in the following steps and also from time periods when sample air is not present in the chamber.

In the purge mode the controller 20 deactivates the aspirator 14 (step 3). The aspirator 36 is then activated to draw air through the filter 34 and drive clean, filtered, air toward the detection chamber 12. The detection chamber 12 is thereby purged of sample air and filled with clean air. The aspirator 14 is of a type that, when deactivated, allows air to pass through. As the chamber 12 is purged air escapes the chamber 12 via the outlet 38 and travels toward (or through) aspirator 14 and pipe network 30. Air also escapes the chamber 12 via the inlet 24.

In this embodiment the aspirator 36 remains active for 30 seconds to ensure that the detection chamber is fully purged of sample air (step 4) before further steps are performed. This is referred to the 'measure background start delay'. The controller 20 monitors the electrical current (in particular the current pulses) drawn by the aspirator 36. Based on the drawn electrical current the controller 20 can make an inference of the operational condition of the aspirator (step 5). Alternatively, the aspirator 36 may have a tachometer output connected to the controller 20. If the aspirator 36 is not running, or is not running correctly, a fault signal is generated (step 13).

The controller 20 then records the indicative signal 16 i.e. 'reads smoke level' at intervals (in this embodiment 1 second intervals) for a 'measure background average time' (in this embodiment for eight seconds) whilst the chamber 12 is filled with clean air (step 6). The eight seconds of stored indicative signal is averaged to produce a new measure of background light. Statistical measures of the signal (eg standard deviation, maximum deduction) are also calculated.

If the new measure of background light is more than a predetermined threshold (step 7C) a fault signal is generated (step 14A). Similarly if the new measure of background light is too low a fault signal is generated. If the stored indicative signal (or alternatively the continuous indicative signal during the purge mode) is too erratic, e.g. a standard deviation or an RMS noise level are more than a predetermined threshold or a maximum deviation from the average signal of more than a predetermined threshold, a fault signal is generated (steps 7A and 7B).

In the event of a fault signal, the background is not reset and the fault is recorded in a log (step 14B).

If no fault signal is generated, the new measurement of background light is substituted for the old, and the logic applied by the controller 20 is so adjusted (step 8). An event log stored within the controller 20 records that the measurement of background light has been updated (step 9).

After the logic of the controller is adjusted the aspirator 36 is deactivated and the aspirator 14 activated to establish airflow through the detector 10 as in the detecting, mode (step 10) and the purge mode comes to an end. A period referred to as 'measure background restart time' (15 seconds in this embodiment) is allowed for the relative amounts of sample and clean air in the detection chamber, and the flow patterns therein, to return to steady state (step 11) before the controller reverts to the detecting mode (steps 12A and 12B). As such, step 11 can be viewed as a transitional mode between the detecting mode and the purge mode.

In the desired embodiment, statistical measures are calculated and considered and the background updated (steps 7A to 9) in the purge mode. It will be appreciated that these steps might occur at some other time, e.g. during the detecting or transitional modes.

Figure 6:
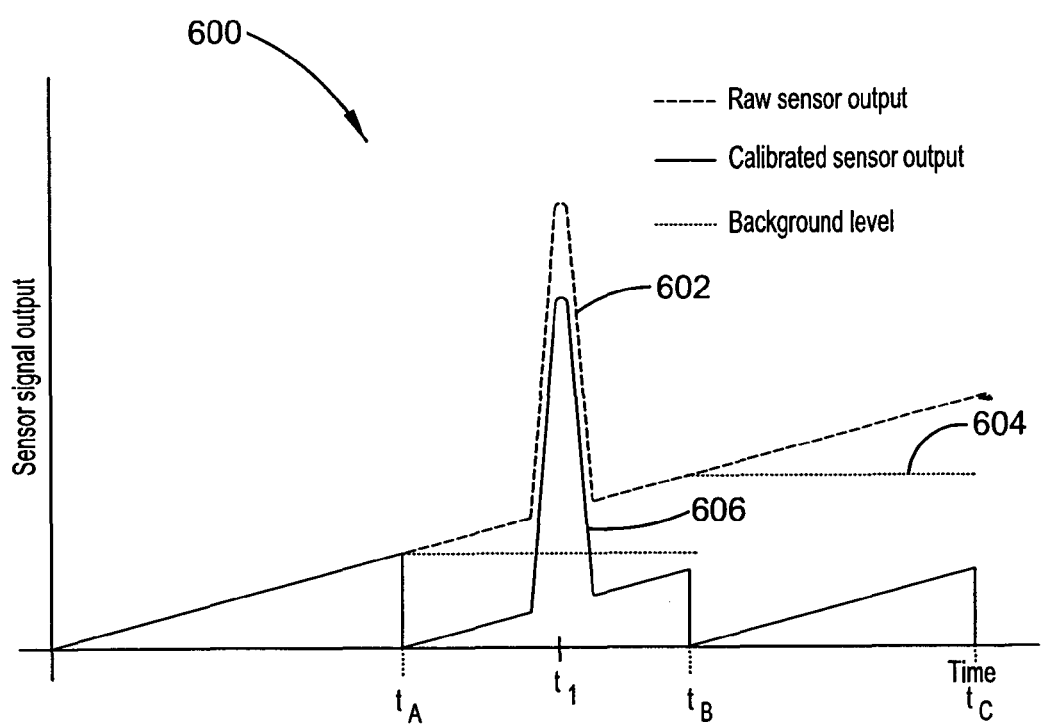
FIG. 6 illustrates a graph of sensor output and corrected output over time illustrating the operation of a method in accordance with an embodiment of the present invention.

Preferred embodiments of the invention thereby provide for the efficient calibration of a particle detector and the efficient compensation for accumulation of dust and debris in the detection chamber. FIG. 6 illustrates a graph 600 of a raw sensor output and calibrated sensor output over time illustrating the operation of a method in an embodiment of the present invention.

FIG. 6 illustrates schematically the following three quantities plotted over time to illustrate graphically how an embodiment of the invention operates:

A plot of the raw sensor output 602. This quantity reflects the level of scattered light being received at a light sensor of the detection chamber over time. As can be seen this plot has a generally upward trend over time. This trend is caused by an increase in background light in the chamber resulting from an increase in level of reflection off the chamber walls. This reflection is caused by the accumulation of dust etc. on the chamber walls. The peak centred at $t_1$ illustrates a temporary peak in received light caused by the detection of a fire event.

A plot 604 of the Background 604 that is used to correct the Raw sensor output over time. As can be seen the plot 604 includes a series of segments which extend between purge event times. This example illustrates three purge events at times $t_A$, $t_B$ and $t_C$. At each time $t_A$, $t_B$ and $t_C$ the detector goes into purge mode, flushes the chamber with clean air, and detects a the light level in the chamber in the presence of clean air. This value is then set as the background level 604 and is used until the next purge process take place.

A corrected sensor output 606. This value 606, in its simplest form represents the value of the raw sensor output with the current background value subtracted from it.

Figure 3:
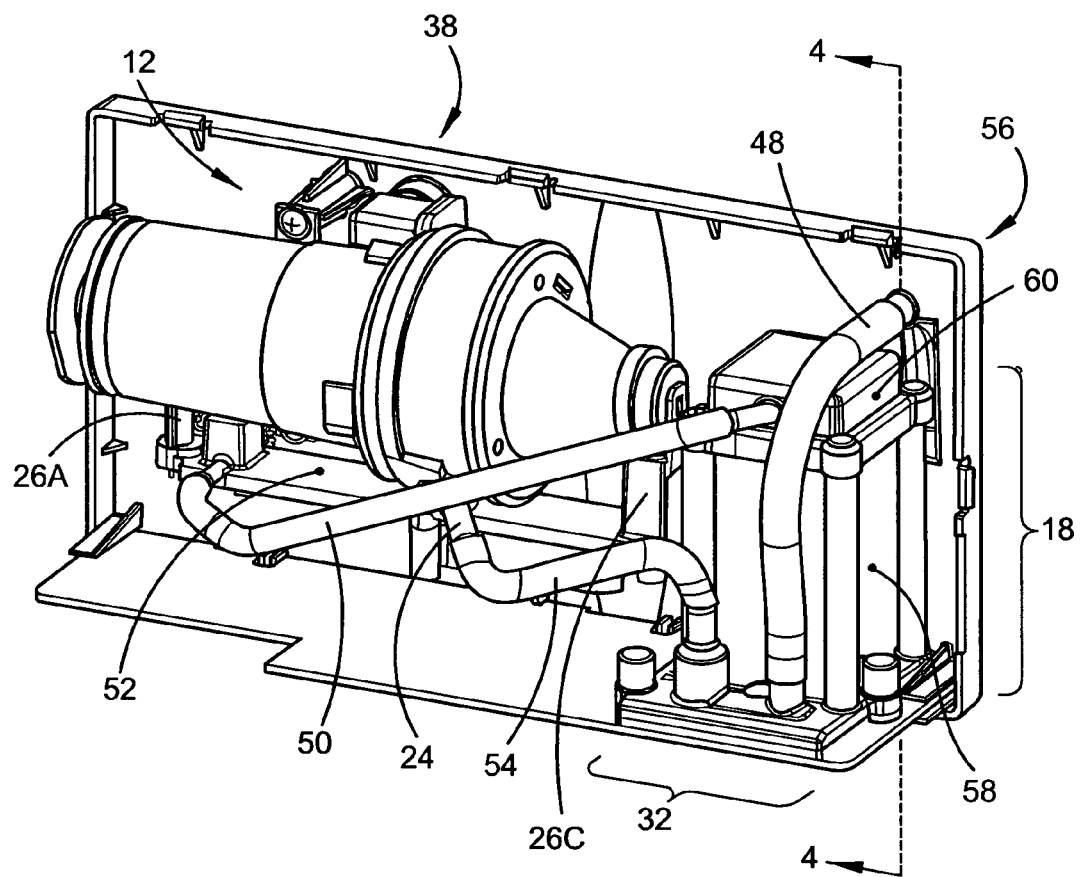
FIG. 3 is a perspective view of the detection chamber, clean air supply and plumbing fitting of the particle detector of FIG. 1.
Figure 4:
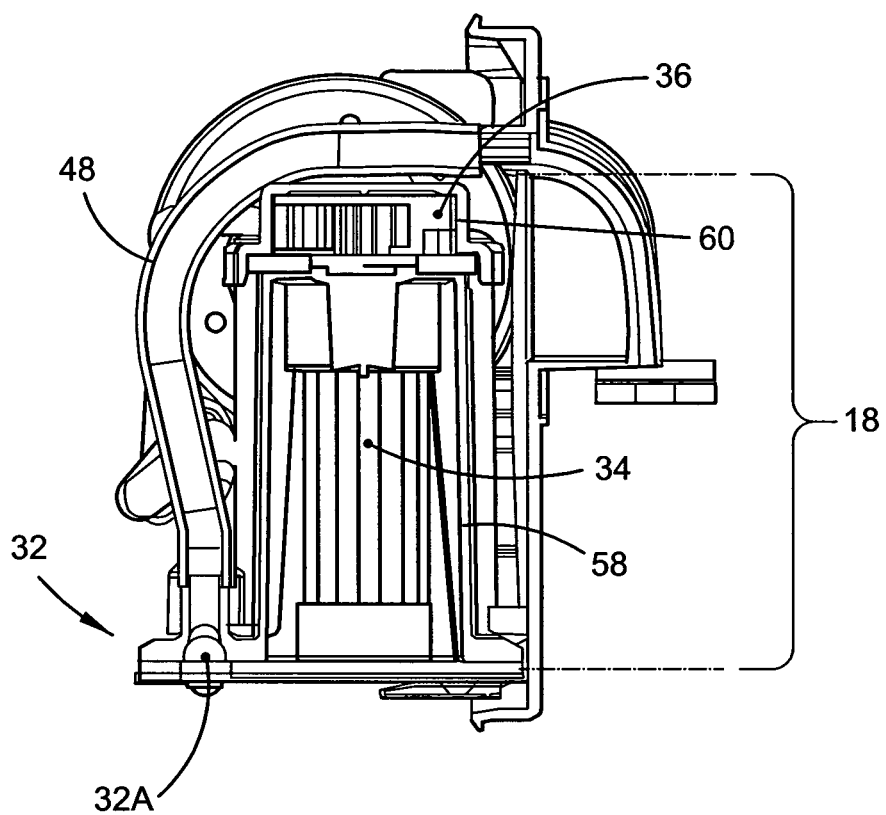
FIG. 4 is a transverse cross section view corresponding to the line 4-4 in FIG. 3.

FIGS. 3 and 4 illustrate the structure of components of a preferred embodiment of the. detector.

In the detecting mode air is received via an inlet 56 at the rear of the detector and conveyed to the plumbing fitting 32 by pipe 48. Air leaves the detector via outlet 38 at the rear of the detector. Aspirator 14 (not shown in FIGS. 3 and 4) creates a pressure differential between the inlet 56 and the outlet 38 to move air through the detector.

A portion of the plumbing fitting 32 is integrally formed with a housing 58 which also forms a portion of the clean air supply 18. The plumbing fitting 32 includes a manifold space 32A. The manifold space 32A is broadly T-shaped, including two opposed arms and single central arm, and lies in a horizontal plane. A nipple in the form of an upstanding tubular spigot is positioned at the end of each of the opposed arms of the "T".

One of the tubular spigots is sealing received within an end of the pipe 48 to receive air into the manifold space 32A. The other of the tubular spigots is sealing received within an end of a pipe 54 to deliver sample air to the detection chamber 12. The central arm of the "T" opens into the interior of the housing 58 to supply air to the clean air supply 18.

The housing 58 is an upstanding tubular structure of square cross section. The housing 58 is mounted on plate, which plate closes housing 58 and defines the lower extent of the manifold space 32A. The filter 34 consists of a permeable wall defining a tubular structure that sits concentrically within the housing 58. Air received into the interior of the housing 58 from the plumbing fitting 32 is filtered as it passes through the permeable wall into an interior of the filter 34.

The aspirator 36 rotates about a vertical axis and sits atop filter 34 to draw air from the interior of the filter. A lid 60 overlies the aspirator and mates with, and thereby closes, the housing 58. A nipple in the form of a tubular spigot projects obliquely forward, in a horizontal plane, from a side wall of the lid 60 and is sealing received within an end of pipe 50. The other end of pipe 50 sealing communicates with a manifold 52. The manifold 52 communicates with the inlets 26A, 26B and 26C.

In certain embodiments: the pipe 54, which connects the plumbing fitting 32 and sample air inlet 24, is long and thin to control the impedance of the sample air flow path; and respective narrow apertures are positioned between filter 34 and aspirator 36 and within manifold 52 at positions corresponding to each of the inlets 26A, 26B and 26C to control the impedance of the clean air flow path. The relative impedance of the two flow paths is thereby balanced so that appropriate proportions of clean and sample air are delivered to the detection chamber when in the normal, detection, mode.

According to the described embodiment, aspirator 14 draws air from the pipe network 30 and the outlet 38 of the detection chamber 12. This arrangement is referred to as a sub-sampling loop. According to other embodiments, the aspirator draws air only from the detection chamber and the plumbing fitting receives air directly from the piping network rather than from the aspirator exhaust. These other embodiments suffer drawbacks including a significantly increased transit time from the pipe network to the detector.

As will be appreciated, embodiments of the present invention could use multiple detection chambers, either with shared or separate main aspirators; and/or shared or separate clean air aspirators. All of these alternative embodiments constitute aspects of the invention.

It will be understood that the invention disclosed and defined in this specification extends to all alternative combinations of two or more of the individual features mentioned or evident from the text or drawings. All of these different combinations constitute various alternative aspects of the invention.

The claims defining the invention are as follows:

1. A particle detector including:
   a chamber including at least one sample inlet for receiving sample fluid, at least one clean fluid inlet for receiving clean fluid, and at least one fluid outlet;
   a first aspirator for moving the sample fluid through the chamber;
   a light source for projecting a light beam through the chamber;
   one or more sensors for detecting, and providing a sensor signal indicative of, particles in the chamber, wherein the one or more sensors have a field of view intersecting the projected light such that the one or more sensors receive light scattered from the projected light beam by particles in the chamber;
   a controller having a detecting mode and a purge mode;
   a clean fluid supply for supplying clean fluid to the clean fluid inlet, the clean fluid supply and clean fluid inlet cooperating, when in the detecting mode, to direct clean fluid into the chamber to prevent contamination by dust and debris of one or more components, the contamination of which would reduce the accuracy of the particle detector; and
   the controller, when in the detecting mode, receiving the sensor signal and applying logic to the sensor signal to generate a further signal, and when in the purge mode controlling substantial purging of the chamber of sample fluid with clean fluid from the clean fluid supply;
   the controller receiving the sensor signal while the chamber is purged with clean fluid from the clean fluid supply and if necessary adjusting the logic in response thereto, to reduce false alarms due to accumulation of dust and debris in the chamber.

2. The detector of claim 1 wherein the clean fluid supply includes a filter, for filtering fluid to produce clean fluid, and a dedicated clean fluid aspirator for moving the clean fluid, the dedicated clean fluid aspirator being downstream of the filter to avoid exposure to unfiltered fluid.

3. The detector of claim 2 wherein, when in the detecting mode, the dedicated clean fluid aspirator is inactive and the first aspirator moves fluid through the filter.

4. The detector of claim 2 further including plumbing for dividing a stream of fluid into two or more portions, and directing one portion to the clean fluid supply to be filtered to form clean fluid, and directing another portion to the chamber to form the sample fluid.

5. The detector of claim 1 wherein the controller is configured to deactivate the first aspirator when in the purge mode.

6. The detector of claim 1 wherein the controller is configured to automatically enter the purge mode periodically.

7. The detector of claim 1 wherein the detector is an optical particle detector.

8. The detector of claim 1 being a smoke detector.

9. The detector of claim 1 wherein the logic includes an alarm threshold.

10. The detector of claim 1 wherein the controller is configured such that a transition from the detection mode to purge mode is conditional on the sensor signal.

11. The detector of claim 1 wherein the logic includes subtracting a measure of background light from the sensor signal and the adjusting the logic includes updating the measure of background light.

12. The detector of claim 1 which further includes at least one valve for preventing sample fluid entering the at least one sample inlet of the chamber when the detector is in the purge mode, and allowing sample fluid to enter the at least one sample inlet of the chamber when the detector is in the detecting mode.

13. The detector of claim 12 wherein the first aspirator additionally causes the clean fluid supply to enter the chamber.

14. A particle detector including:
   a chamber including at least one sample inlet for receiving sample fluid, and at least one fluid outlet;
   a first aspirator for moving the sample fluid through the chamber;
   a light source for projecting a light beam through the chamber;
   one or more sensors for detecting, and providing a sensor signal indicative of, particles in the chamber, wherein the one or more sensors have a field of view intersecting the projected light such that the one or more sensors receive light scattered from the projected light beam by particles in the chamber;
   a clean fluid supply, the clean fluid supply including a filter, for filtering fluid to produce clean fluid, and a dedicated clean fluid aspirator for moving the clean fluid, the dedicated clean fluid aspirator being downstream of the filter to avoid exposure to unfiltered fluid; and
   a controller having a detecting mode and a purge mode;
   the controller,
      when in the detecting mode, receiving the sensor signal and applying logic to the sensor signal to generate a further signal, and
      when in the purge mode controlling substantial purging of the chamber of sample fluid with clean fluid from the clean fluid supply;
   wherein the controller receives the sensor signal while the chamber is purged with clean fluid from the clean fluid supply, and if necessary adjusts the logic in response thereto, to reduce false alarms due to increased light scattering from dust and debris that has accumulated in the chamber.

15. The detector of claim 14 wherein, when in the detecting mode, the dedicated clean fluid aspirator is inactive and the first aspirator moves fluid through the filter.

16. A method of operating a particle detector;
   the particle detector including:
   a chamber having:
   at least one sample inlet for receiving sample fluid,
   at least one clean fluid inlet for directing clean fluid into the chamber to prevent contamination by dust and debris of one or more components the contamination of which would reduce the accuracy of the particle detector, and
   at least one fluid outlet;
   a light source for projecting a light beam through the chamber; and one or more sensors for detecting, and providing a sensor signal indicative of, particles in the chamber, wherein the one or more sensors have a field of view intersecting the projected light such that the one or more sensors receive light scattered from the projected light beam by particles in the chamber;

the method including when in a detecting mode:
moving sample fluid through the chamber;
receiving the sensor signal to detect particles in the chamber; and
applying logic to the sensor signal to generate a further signal; and when in a purge mode:
substantially purging the chamber of sample fluid with clean fluid via the clean fluid inlets; and
receiving the sensor signal while the chamber is purged with clean fluid from the clean fluid supply; and
if necessary adjusting the logic in response thereto, to reduce false alarms due to contamination by dust and debris.

17. The method of claim 16 further including moving fluid through a filter to produce the clean fluid.

18. The method of claim 17 wherein said purging includes activating a dedicated clean fluid aspirator, the dedicated clean fluid aspirator being downstream of the filter to avoid exposure to unfiltered fluid.

19. The method of claim 17, further including
dividing a stream of fluid into two or more portions,
directing one of the portions to the filter to be filtered to form the clean fluid, and
directing another of the portions to the chamber to form the sample fluid.

20. The method of claim 16 further including transitioning between purge mode and detecting mode periodically.

21. The method of claim 16 wherein said purging is conditional on the sensor signal being below a predetermined threshold.

22. The method of claim 16 wherein the
detector includes a first aspirator for moving sample fluid through the chamber; and
the purging includes deactivating the first aspirator.

23. The method of claim 16 wherein the particle detector is an optical detector.

24. The method of claim 16 wherein the particle detector is a smoke detector.

25. The method of claim 16 wherein the logic includes an alarm threshold.

26. The method of claim 16 wherein the logic includes subtracting a measure of background light from the indicative signal and the adjusting the logic includes updating the measure of background light.

27. A method of operating a particle detector;
the particle detector including:
a chamber including at least one sample inlet for receiving sample fluid and at least one fluid outlet;
a light source for projecting a light beam through the chamber;
one or more sensors for detecting, and providing a sensor signal indicative of, particles in the chamber, wherein the one or more sensors have a field of view intersecting the projected light such that the one or more sensors receive light scattered from the projected light beam by particles in the chamber; and
a clean fluid supply, the clean fluid supply including a filter, for filtering fluid to produce clean fluid, and a dedicated clean fluid aspirator for moving the clean fluid, the dedicated clean fluid aspirator being downstream of the filter to avoid exposure to unfiltered fluid;

the method including when in a detecting mode:
moving sample fluid through the chamber;
receiving the sensor signal to detect particles in the chamber; and
applying logic to the indicative signal to generate a further signal; and when in a purge mode:
substantially purging the chamber of sample fluid with clean fluid from the clean fluid supply; and
receiving the sensor signal while the chamber is purged with clean fluid from the clean fluid supply; and
if necessary adjusting the logic in response thereto, to reduce false alarms due to increased light scattering from dust and debris that has accumulated in the chamber.

* * * * *